US006558626B1

(12) United States Patent
Aker et al.

(10) Patent No.: US 6,558,626 B1
(45) Date of Patent: May 6, 2003

(54) VAPOR SENSING INSTRUMENT FOR ULTRA TRACE CHEMICAL DETECTION

(75) Inventors: Craig A. Aker, Stillwater, OK (US); Colin J. Cumming, Stillwater, OK (US); Mark E. Fisher, Stillwater, OK (US); Michael J. Fox, Glencoe, OK (US); Marcus J. laGrone, Cushing, OK (US); Dennis K. Reust, Stillwater, OK (US); Mark G. Rockley, Stillwater, OK (US); Eric S. Towers, Stillwater, OK (US)

(73) Assignee: Nomadics, Inc., Stillwater, OK (US)

( * ) Notice: Subject to any disclaimer, the term of this patent is extended or adjusted under 35 U.S.C. 154(b) by 0 days.

(21) Appl. No.: 09/978,491

(22) Filed: Oct. 16, 2001

Related U.S. Application Data
(60) Provisional application No. 60/241,068, filed on Oct. 17, 2000.

(51) Int. Cl.[7] ............................................... G01N 21/64
(52) U.S. Cl. ...................... 422/91; 422/82.08; 436/106; 436/172
(58) Field of Search ............................... 422/91, 82.08, 422/82.11; 436/106, 107, 110, 172, 167; 250/458.1, 459.1

(56) References Cited

U.S. PATENT DOCUMENTS

| 4,604,706 A | 8/1986 | Fisher, Jr. et al. |
| 4,645,814 A | 2/1987 | Grubbs et al. |
| 4,715,726 A | 12/1987 | Tsuruta |
| 5,026,783 A | 6/1991 | Grabbs et al. |
| 5,082,630 A | 1/1992 | Partin et al. |
| 5,157,261 A | * 10/1992 | Grey et al. ............... 250/458.1 |
| 5,414,069 A | * 5/1995 | Cumming et al. ........... 528/310 |
| 5,453,220 A | 9/1995 | Swager et al. |
| 5,519,147 A | 5/1996 | Swager et al. |
| 5,597,890 A | * 1/1997 | Jenekhe ....................... 528/377 |
| 5,728,584 A | * 3/1998 | Sausa et al. ................. 436/106 |
| 6,085,576 A | 7/2000 | Sunshine et al. |
| 6,245,576 B1 | * 6/2001 | Hiley ........................... 436/110 |
| 6,477,907 B1 | * 11/2002 | Chambers et al. ............. 73/866 |

* cited by examiner

*Primary Examiner*—Jeffrey Snay
(74) *Attorney, Agent, or Firm*—Dunlap Codding & Rogers (57) ABSTRACT

A detector for detecting vapors emitted from energetic compounds includes a housing, a pump and a sensing assembly. The housing has an inlet, an outlet and an enclosed sensing volume there between. The pump communicates with the housing for moving a carrier gas sequentially through the enclosed sensing volume at a predetermined flow rate. The sensing assembly senses the vapors of the energetic compound delivered by the carrier gas as the carrier gas passes through the housing. The sensing assembly includes a sensing unit constructed of an amplifying fluorescent polymer, a source of excitation, a light detector, and a convertor assembly.

23 Claims, 3 Drawing Sheets

VAPOR SENSING INSTRUMENT FOR ULTRA TRACE CHEMICAL DETECTION

CROSS REFERENCE TO RELATED APPLICATIONS

The present patent application claims benefit of provisional patent application identified by U.S. Ser. No. 60/241,068 filed on Oct. 17, 2000, the entire content of which is hereby incorporated herein by reference.

STATEMENT REGARDING FEDERALLY SPONSORED RESEARCH OR DEVELOPMENT

Not Applicable.

BACKGROUND OF THE INVENTION

Landmine detection is a tedious, time consuming, dangerous and expensive task. Perhaps a hundred million land mines are presently deployed on earth, notably in underdeveloped countries which scarcely have the resources to remove them. Hence, the development of technologies which can expedite landmine removal are in demand. For instance, the United States government has initiated a "Dog's Nose Research Program" through the Defense Advanced Research Projects Agency (DARPA). The purpose of the program is to study the ability of dogs to smell and identify vapors emanating from land mines, and to develop a chemical sensor of comparable sensitivity.

Many chemical sensors that detect explosives use secondary detection to infer the presence of target analytes. In secondary detection techniques, a sequence of chemical or other events must be initiated by the analyte molecule before the change can be transduced into an electrical signal. A simple example of a secondary detection technique would be one in which the analyte of interest, such as TNT, reaches a surface where it is decomposed into nitrous or nitric oxide ($NO_x$, a chemical reaction product). This $NO_x$ is then subsequently detected by its ability to quench an emitting material. Another secondary detection method for explosives uses fluorescently labeled antibodies. The fluorescent antibody is attached to a substrate, and when explosives attach to the substrate, the fluorescent tag is displaced, being released into a stream of water. A fluorescence detector then detects the displaced fluorescent tag downstream in the flowing water, rather than detecting the actual analyte molecule directly. Yet another method for detecting explosives is disclosed in U.S. Pat. No. 5,082,630, entitled "Fiber Optic Detector For Immuno-Testing" issued to Partin et al on Jan. 21, 1992, which discloses a method for determining the presence of specific chemicals in air by exchanging the target chemical for a fluorescently-tagged antigen that is bound to an antibody. However, these detection methods are indirectly sensing the target analyte, and each step in a secondary detection scheme lowers the overall efficiency of the detection process. Therefore, there exists a need in the art for a detector which can directly sense the presence of a target analyte, thereby improving the efficiency of detection of analyte and reducing the potential for loss and interference, thereby overcoming the disadvantages and defects of the prior art.

BRIEF DESCRIPTION OF THE DRAWINGS

Shown in FIG. 1A is a schematic drawing of the structure of an amplifying fluorescent polymer used in accordance with the present invention.

Shown in FIG. 1B is a schematic drawing of the structure of an amplifying fluorescent polymer used in accordance with the present invention.

Shown in FIG. 2 is a diagrammatic representation of a detector constructed in accordance with the present invention.

Shown in FIG. 3 is a cross-sectional view of a sensing zone taken along the lines 3—3 in FIG. 2.

Shown in FIG. 4 is a cross-sectional view of an adsorption/desorption zone taken along the lines 4—4 in FIG. 2.

Shown in FIG. 5 is a cross-sectional view of an equilibrium zone taken along the lines 5—5 in FIG. 2.

Shown in FIG. 6 is a cross-sectional view of the chromatography zone taken along the lines 6—6 in FIG. 2.

Shown in FIG. 7 is a cross-sectional view of the preconditioning zone taken along the lines 7—7 in FIG. 2.

DETAILED DESCRIPTION OF THE INVENTION

Certain molecules absorb photons of light of a certain wavelength and then emit a photon of light of a longer wavelength. This emission of light is known as fluorescence. Traditional fluorescence detection schemes measure a change in fluorescence intensity when a molecule of analyte interacts with a single fluorescent probe molecule. A photon of light must be absorbed by the fluorescent probe molecule while a molecule of analyte is interacting with the probe molecule. When the analyte molecule interacts with the fluorescent probe molecule, either an increase or decrease in the intensity of fluorescence is observed. "Emissive Polymers and Devices Incorporating These Polymers", U.S. Ser. No. 60/084,247, filed on May 5, 1998 the entire content of which is hereby expressly incorporated herein by reference, describes a method for sensing an analyte through the luminescent and conductive properties of a class of polymer compositions which are referred to herein as amplifying fluorescent polymers.

The backbone of amplifying fluorescent polymers (AFP) are made up of alternating multiple chemical bonds, forming a conjugated polymer backbone that extends the length of the polymer chain. Absorption of a single photon of light produces an exciton (an excited-state electron) that migrates along the polymer backbone and also between polymer chains in solid phase films of the polymer. As the exciton migrates through the polymer, if it encounters an analyte molecule bound to one of many receptor sites on the polymer molecule, the exciton is trapped and no fluorescence from the photon absorption event results. This process is referred to as fluorescence quenching. In this way, the exciton formed from absorption of a single photon of light by the amplifying fluorescent polymer has many opportunities to encounter an analyte molecule bound to any of a number of receptor sites encountered by the exciton. By contrast, in traditional fluorescence sensing schemes, the excited state electron is confined to the absorbing fluorescent probe molecule, thereby "sampling" only one 'receptor site'. Because the exciton in an amplifying fluorescent polymer can sample many receptor sites, the number of receptor sites sampled per photon absorbed is greatly increased compared with a monomeric chromophoric system. This increases the detection sensitivity for target analytes significantly, accounting in part for the extraordinary sensitivity of the amplifying fluorescent polymer materials as sensory materials. In addition, the receptor sites on the amplifying fluorescent polymer are carefully designed and synthesized to preferentially bind to only certain types of molecules. This increases the selectivity of the amplifying fluorescent polymer so that it preferentially senses a narrow class of chemical compounds, rather than responding to many chemical analytes.

The present invention is related to a detector for detecting vapors emitted from energetic compounds present in a sample. The term "energetic compound" may be used interchangeably herein with the terms "Aanalyte" and "explosive related compound". Examples of energetic compounds or explosive related compounds which may be detected by the present invention include 2,4,6-Trinitrotoluene (TNT); 1,3,5-Trinitrobenzene (TNB); 2,4,6-Trinitro-m-xylene (TNX); 2,4,6-Trinitrochlorobenzene (picryl chloride); 2,4,6-Trinitrophenol (picric acid); ammonium picrate (Explosive D); 2,4,6-Trinitro-m-cresol (TNC); 2,4,6-Trinitroresorcinol (styphnic acid); 2,4,6-Trinitroanisole (TNA, methyl picrate); 2,4,6-Trinitrophenetole (TNP, ethyl picrate); 2,4,6-Trinitroaniline (picramide, 1-monoamino-2,4,6-trinitrobenzene, MATB); 1,3-Diamino-2,4,6-trinitrobenzene (DATB); 1,3,5-Triamino-2,4,6-trinitrobenzene (TATB); and 2,4,6,N-Tetranitro-N-methylaniline (tetryl, 2,4,6-trinitrophenylmethyinitramine). Examples of other substances that may be detected by the present invention include, but are not limited to, 2-amino-4,6-dinitrotoluene, 4-amino-2,6-dinitrotoluene, 2-amino-4-nitrotoluene, 3,5-dinitroaniline, 1,3-dinitrobenzene, 2,4-dinitrotoluene, 3-nitroaniline, and 2,4,6-trinitroaniline.

Figure 2:
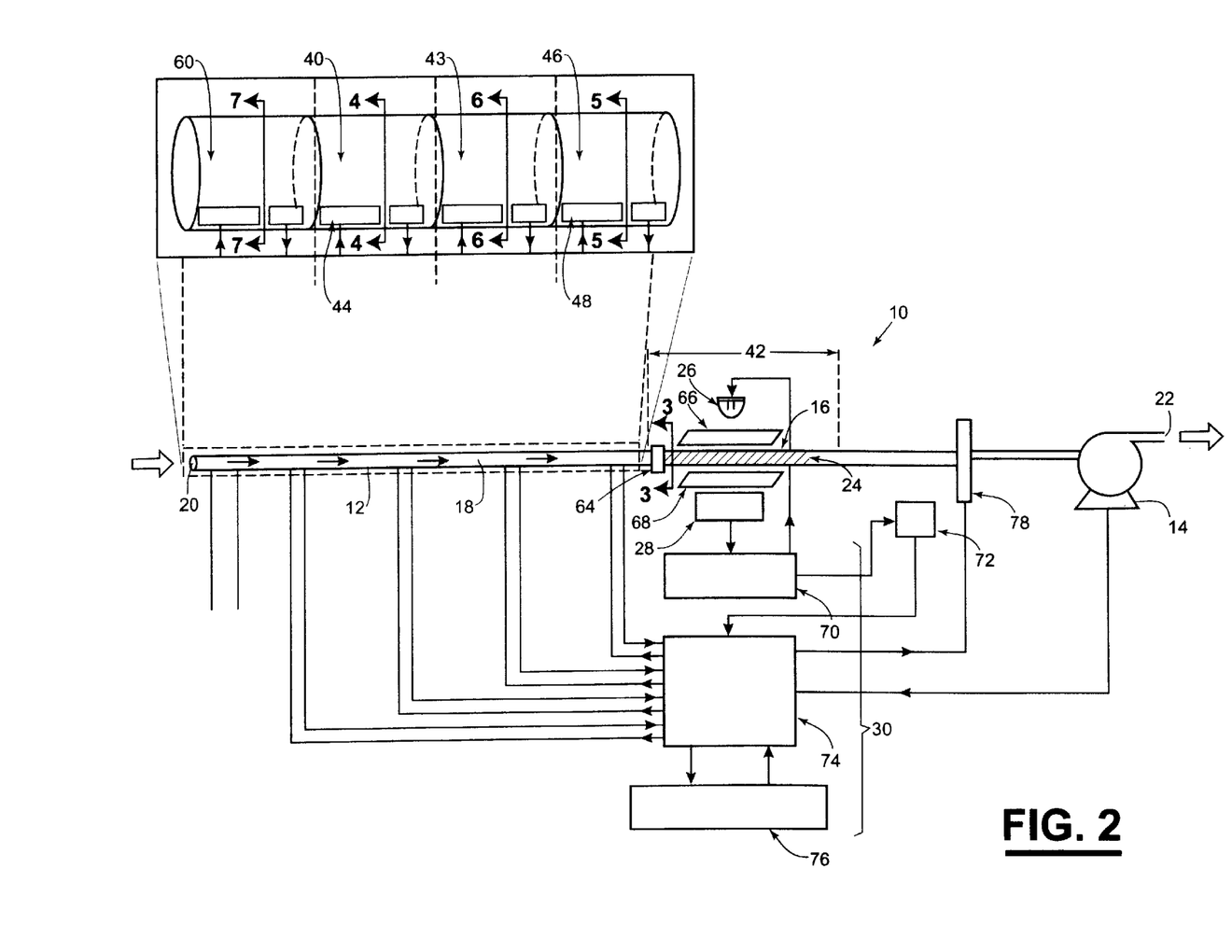

Shown in FIG. 2 is a detector 10 constructed in accordance with the present invention. Broadly, the detector 10 comprises a housing 12, a pump 14, and a sensing assembly 16. The housing 12 defines an enclosed sensing volume 18, and the housing 12 is also provided with an inlet 20 and an outlet 22 which communicates with the enclosed sensing volume 18 such that a carrier gas can be moved sequentially through the inlet 20, the enclosed sensing volume 18 and the outlet 22. The pump 14 communicates with the housing 12 for moving the carrier gas sequentially through the inlet 20, the enclosed sensing volume 18 and the outlet 22 at a predetermined flow rate. The sensing assembly 16 senses vapors of the energetic compound delivered by the carrier gas as the carrier gas passes through the housing 12. The sensing assembly 16 comprises a sensing unit 24 constructed of an amplifying fluorescent polymer positioned in the housing 12 so as to be openly communicating with the enclosed sensing volume 18 of the housing 12, wherein the intensity of light emitted by the amplifying fluorescent polymer varies in response to interaction of the amplifying fluorescent polymer with the molecules of the energetic compound delivered by the carrier gas. The sensing assembly 16 further comprises a source of excitation 26 producing a medium that interacts with the amplifying fluorescent polymer to cause the amplifying fluorescent polymer to generate light and a light detector positioned to receive the light generated by the amplifying fluorescent polymer, wherein the light detector 28 outputs a signal indicative of the intensity of the light generated by the amplifying fluorescent polymer. Such signal is received by a converter assembly 30 of the sensing assembly 16, and the convertor assembly 30 converts the signal from the light detector 28 into a format perceivable by an individual.

The amplifying fluorescent polymer provides the detector 10 with a means If or decreasing the number of analyte molecules required in order for a fluorescent quenching event to be sensed by the sensing assembly 16. The binding of one analyte molecule to the amplifying fluorescent polymer quenches the emission of many polymer repeat units. When an analyte of interest lands on a polymer binding site, many polymer repeat units in the vicinity of the bound analyte do not emit the absorbed light as fluorescence. As a result, the polymer fluorescence is said to be "quenched" by the adsorption of the analyte molecule.

The number of binding sites per amplifying fluorescent polymer chain is very large. The analyte may attach to any one of the binding sites to effect quenching of the emission from many polymer repeat units. Therefore, one absorbed photon can "sample" a much larger spatial region testing for the arrival and adsorption of an analyte molecule. By contrast, if a simple donor chromophore was excited by that same photon instead of the amplifying fluorescent polymer, the exciton would be trapped inside the spatial confines of that monomer or simple molecule. The spatial region sampled by the exciton in the case of the monomer would be quite small compared with the spatial region sampled in the case of the amplifying fluorescent polymer. The likelihood that the analyte molecule would land on this smaller spatial region while some fraction of the photon energy is still present in the chromophore is then diminished by comparison with the amplifying fluorescent polymer in strict proportion to the ratio of the space sampled by the excited electron generated through absorption of the photon.

Figure 1A:
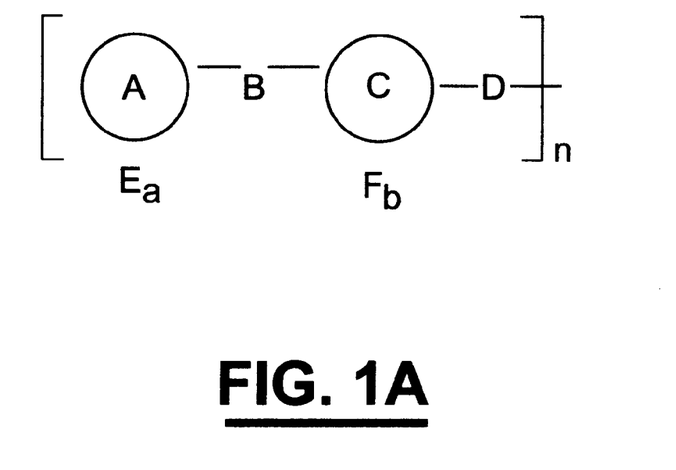

Examples of amplifying fluorescent polymers which can be utilized in accordance with the present invention have been disclosed in "Emissive Polymers and Devices Incorporating These Polymers", which is incorporated herein by reference. The structure for the amplifying fluorescent polymer is given in FIG. 1A, wherein A and C are aromatic groups and B and D are selected from the group consisting of a carbon-carbon double bond and a carbon-carbon triple bond. Any hydrogen on aromatic group A and C can be replaced by E and F respectively, a and b being integers which can be the same or different and a=0–4, b=0–4 such that when a=0, b is nonzero and when b=0, a is nonzero, and at least one of E and F includes a bicyclic ring system having aromatic or non-aromatic groups optionally interrupted by O, S, $NR^1$ and $C(R^1)_2$, wherein $R^1$ is selected from the group consisting of hydrogen, $C_1$–$C_{20}$ alkyl, $C_1$–$C_{20}$ alkoxy and aryl. The value n is less than about 10,000.

Figure 1B:
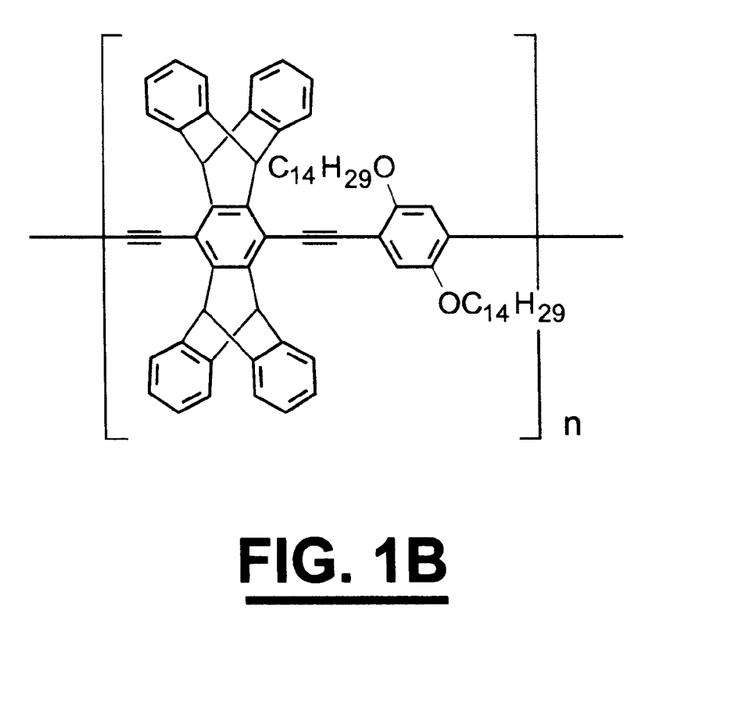

Such amplifying fluorescent polymers are capable of emitting radiation and exhibiting relatively long luminescent lifetimes and relatively high quantum yields. These materials also contain structures that prevent undesirable δ-stacking interactions between backbones of adjacent polymer molecules. "Emissive Polymers and Devices Incorporating These Polymers" discloses a genus containing a multitude of species of amplifying fluorescent polymers. In a preferred embodiment, the present invention is directed to the use of polyarylene ethynylenes, such as is shown in FIG. 1B, as amplifying fluorescent polymers in a detector for detecting vapors emitted from an energetic compound. However, the invention is not limited to the use of polyarylene ethynylenes as the amplifying fluorescent polymer, as the invention is not limited to finding land mines or nitroaromatic compounds. Rather, the invention is designed to be adapted to detect other analytes by changing the amplifying fluorescent polymers in the housing 12. In addition, amplifying polymer blends may also be used as the amplifying fluorescent polymer. Some blends exhibit enhanced energy transfer and sensitivity relative to the individual polymers while others exhibit light output exceeding the sum of the light outputs from the separate polymers when not in a mixture. Amplifying fluorescent polymers may also be blended with other non-amplifying polymers. Examples of non-amplifying polymers commonly used, but not limited to, are polystyrene, polymethylacrylate, polyvinylcarbazole, and polyvinylanthracene. Such blends may improve sensitivity and response kinetics when blended in the appropriate ratios. Ratios may preferably range from about 1:1 to about 1:10 (repeat units of AFP: repeat units of second polymer). Other non-polymers that may also be used as alternative fluorophores include, but are not limited to, fluorescein, rhodamine, anthracene, Texas Red, Cy3, green fluorescent protein and phycoerythrin.

It has been determined that certain chemical additives to the amplifying fluorescent polymer (including but not limited to a class of chemicals known as plasticizers) have very beneficial effects on the amplifying fluorescent polymer. The term "plasticizing material" or "plasticizer" refers to high-boiling solvents or softening agents which are added to a polymer to facilitate processing or to increase flexibility or toughness. The amplifying fluorescent polymer is prone to slow photochemical degradation when exposed to light. The addition of certain plasticizers to the polymer greatly reduces this adverse effect. The rate of photochemical degradation is a function of the intensity of the light used to excite fluorescence in the polymer (i.e., the brighter the excitation source, the more rapid the degradation rate). The addition of the plasticizer makes it possible to increase the intensity of the excitation source without inducing rapid photodegradation. This makes it possible to use more intense excitation sources, which in turn makes the polymer fluoresce more intensely. This improves the signal to noise ratio of the detection process. In addition, the plasticizers increase the intensity of the baseline fluorescence from the amplifying fluorescent polymer (i.e., amplifying fluorescent polymer formulations containing the plasticizer emit more light at a given excitation light intensity than those that do not contain plasticizer). This is also a beneficial effect, since it also serves to increase the signal to noise ratio of the detection process. The fluorescence intensity of the amplifying fluorescent polymer is also temperature sensitive. When the temperature of the amplifying fluorescent polymer increases, the intensity of emission from the polymer decreases. This effect makes it necessary to maintain the temperature of the amplifying fluorescent polymer at very precisely controlled temperatures, which is difficult in a field transportable device. However, addition of plasticizers reduces the temperature sensitivity of the amplifying fluorescent polymer, making the requirements for temperature control less stringent.

There is also evidence that the addition of plasticizers makes the amplifying fluorescent polymer more sensitive to certain analytes than when the plasticizer is absent. This increased sensitivity is by a sensing mechanism that is different than that normally employed. The amplifying fluorescent polymer used in the sensor undergoes a reduction in emission intensity upon exposure to certain analytes (primarily nitroaromatic explosives), but the second mechanism results in an increase in emission intensity upon exposure to other analytes.

It is suggested that the plasticizer causes increased chain separation, thus diminishing the likelihood of excimer formation. It is further suggested that the excimer is a necessary precursor for photodecomposition, possibly because of the formation of triplet monomer or excimer states which sensitize the production of singlet oxygen, which is a very effective oxidizing agent and may be responsible for the photooxidative decomposition of the polymer. Plasticizers have been observed to stabilize the amplifying fluorescent polymer against thermal variations in the emission intensity and also decrease the sensitivity of the polymer emission to thermal drift. Therefore, the addition of plasticizers constitutes a means for increasing the useful life of the polymer by decreasing the quantum yield of photodecomposition.

Examples of commonly used plasticizers include, but are not limited to, phthalates, phosphates, adipates, sebacates, azelates, and fatty acid esters. Examples of plasticizers which could be added to the amplifying fluorescent polymer include, but are not limited to, dioctyl phthalate, 2,2,4-trimethyl-1,3-pentanediol dibenzoate and pentaerythritol tetrabenzoate.

The ratio of plasticizer to amplifying fluorescent polymer is important. The effects of the plasticizer are minimal at too low of a concentration, but decrease the sensitivity of the device (i.e., the sensing unit 24) at concentrations that are too high. The molar ratio of plasticizing material to amplifying fluorescent polymer may vary, as long as the amplifying fluorescent polymer is able to function in accordance with the present invention. Preferably, the ratio of molecules of plasticizing material to amplifying fluorescent polymer repeat units is in the range of about 7:1 to about 50:1. More preferably, the ratio of plasticizing material to amplifying fluorescent polymer is in the range of about 7:1 to about 20:1 Most preferably, the ratio of plasticizing material to amplifying fluorescent polymer is about 15:1.

In a preferred embodiment, the plasticized amplifying fluorescent polymer is produced by first dissolving the amplifying fluorescent polymer in a solvent, preferably a non-polar organic solvent such as toluene or chloroform. The plasticizer and the amplifying fluorescent polymer should be soluble in the same solvent. The concentration of amplifying fluorescent polymer in the solvent will affect the thickness of the amplifying fluorescent polymer film present in the sensing unit 24 of the housing 12, thereby affecting the sensitivity of the detector 10. The concentration of amplifying fluorescent polymer in the solvent will vary, depending on the exact polymer used and the exact solvent used. However, generally about 1 to about 2 milligrams of amplifying fluorescent polymer will be added to about 1 milliliter of solvent. The mixture will then be mixed by any method known in the art, such as by shaking, stirring or use of an ultrasonic bath. The plasticizer is then added to the mixture at ambient temperature and pressure.

In one embodiment, the housing 12 of the detector 10 may be a capillary, such as a glass capillary tube, which has a small internal diameter. It should be understood that hereafter the housing 12 will be identified as a capillary 13. It should also be understood that although a capillary 13 is one embodiment for the housing 12, the housing 12 may be any structure through which the carrier gas can pass and that is suitable to be used in the present invention. Materials that may be used in the construction of the housing 12, should not irreversibly bind target analyte molecules. Materials such as plastics are unpreferable to be used in the construction of the housing 12 due to their permeability by target analytes. The plastic becomes contaminated with the target analytes which are slowly released over time, thus elevating the background response of the sensor. Significant analyte loss due to diffusion into the plastic can occur. Further, metals that oxidize are also an unpreferable choice as a material for constructing the housing 12. Metal oxides strongly bind to many target analytes, resulting in analyte loss. However, there are metals that are preferred in the present invention. Metals such as gold and some grades of stainless steel may be used. Polished metals are preferred because of the better performance of smooth surfaces due to the lower surface area for the analyte to interact with. Other materials that are preferred for the housing 12 include, but are not limited to, silica glass, pyrex and quartz. In addition, thin layers of materials that render structural materials more inert to undesirable adsorption of target analytes may be applied to certain surface materials making them more suitable for use. For example, alkanethiols are suitable for gold surfaces, alkylsilanes are preferred for glass surfaces and silcosteel may be applied through a proprietary process (Restek) on stainless steel.

The diameter of the capillary 13 is preferably in the range of from about 100 microns to about 1 millimeter. The amplifying fluorescent polymer 32 can be placed on an inside wall or walls 34 of the capillary 13. This results in an extraordinarily efficient means for detection of the analyte, as the target analytes (explosives and explosive-related compounds) interact strongly with the walls 34 of the capillary 13, as described in more detail herein after.

The capillary tube 13, such as a 5 mm OD and 0.53 mm ID borosilicate tube made by Corning, is preferably about 83 mm long. The first end of the capillary tube 13 is used as the sample introduction point, referred to herein as the inlet 20. The inlet 20 is coated with an opaque material for the purpose of reducing the amount of ambient light which enters the system. The opaque coating on the inlet 20 of the capillary tube 13 may preferably be a mirror made to reflect light inside the capillary tube 13 back inside the tube 13 upon striking the mirror. The capillary tube 13 serves as a waveguide for the polymer's fluorescent emission, which is collected from the enclosed sensing volume 18 of the tube 13.

The capillary tube 13 is heated to a stable temperature, such as in the range of from about 30 to about 140° Celsius. Heating the capillary tube 13 prevents moisture condensation on the tube 13 and optical components, and also actively stabilizes the response of the amplifying fluorescent polymer inside against temperature variations caused by ingestion of air samples at varying temperatures. The accuracy of the temperature setting is less important than the thermal stability of the amplifying fluorescent polymer. The temperature of the amplifying fluorescent polymer should preferably vary less than about 0.1° Celsius in order to minimize fluctuations in the emission intensity of the amplifying fluorescent polymer.

The capillary 13 is characterized as having an adsorption/desorption zone 40 and a sensing zone 42, with the sensing zone 42 being downstream from the adsorption/desorption zone 40. The adsorption/desorption zone 40 of the capillar 13 selectively adsorbs and desorbs at least a portion of the molecules of the energetic compound present in the carrier gas, and the sensing unit 24 of the sensing assembly 16 is positioned in the sensing zone 42 of the capillary 13 for detection of the desorbed molecules of the energetic compound.

Figure 3:
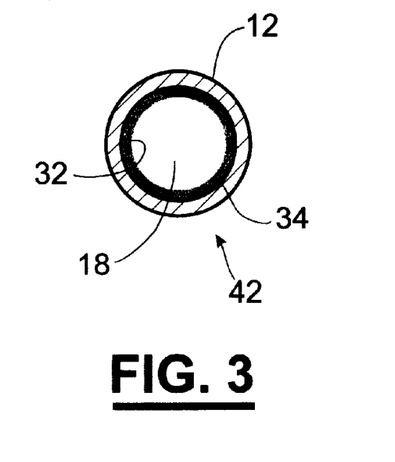

As an inlet carrier gas containing the analyte passes into the bore of the capillary 13 through the inlet 20 and into the adsorption/desorption zone 40, most analytes will have a slight binding interaction with the surface of the adsorption/desorption zone 40 of the capillary 13 through a combination of dispersion forces and/or polar intermolecular forces, and as the analyte encounters the wall 34 of the adsorption/desorption zone 40 of the capillary 13, it is adsorbed onto the wall 34 of the capillary 13 or into the coating of the adsorption/desorption zone 40 of the capillary 13. As a result, when an analyte molecule diffuses to the wall 34 of the adsorption/desorption zone 40 of the capillary 13, its kinetic energy is reduced upon desorption from the surface by comparison with its kinetic energy prior to interaction with the surface. The net effect of this loss in kinetic energy when combined with the proximity of the analyte molecule to the wall itself is a tendency for the molecule to reattach to the wall 34. Molecules of analyte do not normally remain bound to the capillary wall 34 or in the coatings indefinitely, but occasionally desorb from these materials and enter into the carrier gas inside the tube 13. This carrier gas is drawn through the capillary 13, and as the carrier gas passes through the capillary 13, it slowly sweeps the analyte down the length of the tube 13. However, molecules of analyte are swept down the tube 13 only a very short distance before they collide with the wall 34 of the capillary 13 and are readsorbed. This is because after the initial encounter of analyte molecules with the wall 34 of the capillary 13, they on average do not diffuse very far away from the wall 34. Hence, the analyte is extracted from the bulk flow of air through the capillary 13 and is concentrated near the wall 34 of the capillary 13. This process continues as the analyte molecule drifts down the narrow bore capillary tube 13 from the adsorption/desorption zone 40 to the sensing zone 42. The small size of the bore of the capillary 13 has the net effect of concentrating the analyte in the vicinity of the walls 34 of the capillary 13. As shown in FIG. 3, since the amplifying fluorescent polymer 32 is located on the walls 34 of the sensing zone 42 of the capillary 13, the probability that the analyte will interact with the amplifying fluorescent polymer 32 is therefore greatly increased by this tendency for the analyte to concentrate near the walls 34 of the capillary 13. By comparison, if the analyte were not concentrated near the capillary walls 34 as the analyte travels through the adsorption/desorption zone 40, most of the analyte would be swept past the amplifying fluorescent polymer 32 in the sensing zone 42 by the flow of moving carrier gas, never interacting with the amplifying fluorescent polymer 32. If the analyte does not interact directly with the amplifying fluorescent polymer 32, it will not be sensed. Hence, deploying the sensory material (i.e., the amplifying fluorescent polymer) on the wall 34 of the sensing zone 42 of the capillary 13 makes analyte transfer to the sensory material much more efficient, greatly increasing the sensitivity of the detector 10.

The capillary geometry is also a very convenient geometry from which to construct detectors. This geometry makes a number of optical arrangements possible in order to very effectively measure changes in emission from the polymer film.

Figure 4:
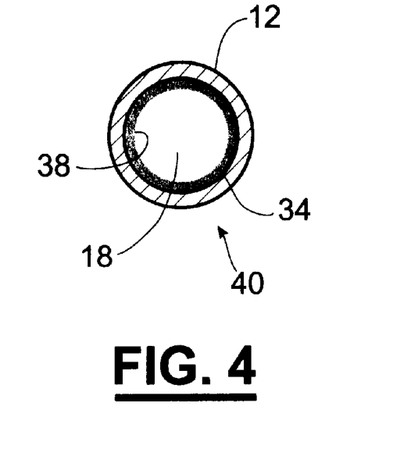

As previously described, analytes are transported down the length of the capillary 13 by the action of the moving carrier gas. Since the analyte interacts with the surface of the capillary 13, the speed with which it moves down the walls 34 of the capillary 13 is related to the strength of the interaction between the analyte and the coating 38 on the surface of the inner wall 34 of the capillary 13 in the adsorption/desorption zone 40, as shown in FIG. 4. Therefore, coating 38 selection is critical. The adsorption/desorption zone 40 is preferably coated with a gas chromatographic stationary phase, such as, but not limited to, dimethylpolysiloxane/diphenylpolysiloxane mixtures or trifluoropropylmethylpolysiloxanes.

As the rate at which the analyte migrates is largely a function of the strength of interaction of the analyte with the coating 38 on the walls 34 of the capillary 13 in the adsorption/desorption zone 40, analytes that have no attraction for the coating 38 are essentially swept down the capillary 13 at the same velocity as the carrier gas. However, analytes that interact strongly with the coating 38 migrate with a velocity much less than that of the carrier gas. Because analytes migrate at rates that are proportional to the strength of interaction with the coating 38, and since the strength of these interactions vary between different chemical analytes, different compounds migrate down the tube at different velocities.

By appropriate selection of the chemical nature of the coating 38 on the inner wall 34 of the capillary 13 in the adsorption/desorption zone 40, the enthalpy of adsorption between the analyte of interest and the coating 38 can be adjusted. The thickness of the coating 38 of the adsorption/desorption zone 40 constitutes an additional variable parameter for control of the interaction time between the analyte and the coated wall of the adsorption/desorption zone 40 of the capillary 13. The analyte will diffuse into the coating 38 of the adsorption/desorption zone 40. As the thickness of the coating 38 of the adsorption/desorption zone 40 increases, the length of time that the analyte molecule spends inside the bulk of the coating 38 of the adsorption/desorption zone 40 prior to desorption from the surface increases. The thickness of the coating 38 may vary, depending on the specific analytes to be detected by the detector 10. However, the thickness of the coating 38 will preferably be in the range of from about 0.25 $\mu$m to about 3 $\mu$m.

The adsorption enthalpy and coating thickness constitute a means for distinguishing between different analytes. This distinction is also a function of the length of the adsorption/desorption zone 40 of the capillary 13 tubing over which the interaction takes place as well as the temperature of the tubing. The four properties, chemical makeup of the coating 38, thickness of the coating 38, temperature of the adsorption/desorption zone, and length of the adsorption/desorption zone 40, define the discrimination between analytes that is made feasible by the use of specific coatings on the inside wall 34 of the capillary 13 in the adsorption/desorption zone 40. By using this discrimination technique prior to the amplifying fluorescent polymer, it is possible to discriminate between explosive related compounds (ERC's) that are highly retained by the adsorption/desorption zone 40 and other volatile organic compounds that are poorly retained by the adsorption/desorption zone 40. In this way, volatile organic compounds which might conceivably quench the emission of the amplifying fluorescent polymer can be discriminated from ERC's.

Each of the lengths of the different zones in the capillary 13 are critical and depend on a number of parameters. The adsorption/desorption zone 40, or "trap zone", must be long enough so that analyte does not bleed through the end of the adsorption/desorption zone 40 during sampling. The rate of analyte migration through the adsorption/desorption zone 40 depends on the affinity of analyte for the coating 38 of the adsorption/desorption zone 40, the temperature of such zone 40, and the flow rate of the carrier gas through such zone 40. Hence, the length of the adsorption/desorption zone 40 will depend on the type of coating used, the temperature of the adsorption/desorption zone 40 during sampling, the flow rate during sampling, and the desired length of the sampling period. Desirably, the length of the adsorption/desorption zone 40 is in the range of from about 2 inches to about 3 inches.

In the detection of explosive related compounds in field conditions, it is common for the detector 10 to ingest compounds other than explosive related compounds which may cause quenching of the amplifying fluorescent polymer. It is desirable to discriminate against these interferents in favor of the explosive related compounds. There are two means by which this can be achieved. The first is the coating 38 in the adsorption/desorption zone 40, which has been described herein before. The second relies upon the sensitivity to temperature of the migration velocity of an analyte across the adsorption/desorption zone 40. The migration velocity is exponentially sensitive to the temperature of the adsorption/desorption zone 40, in part because of the relationship between the binding efficiency of the coating 38 of the adsorption/desorption zone 40 for the analyte and the boiling point of the analyte. An analyte with a low boiling point will tend to be bound less well to the coating in the adsorption/desorption zone 40 than an analyte with a high boiling point. Therefore, by holding the adsorption/desorption zone for a time at a low temperature, low boiling point compounds will tend to travel through the adsorption/desorption zone 40 while high boiling point compounds will be retained. This constitutes a thermal trap. When the temperature of the adsorption/desorption zone 40 is subsequently elevated, the trapped analytes will migrate more quickly through the adsorption/desorption zone 40. By controlling the duration of the trapping cycle and the temperature elevation or 'flash' cycle, it is possible to increase the discrimination between interferents (quenching analytes that are not explosive related compounds) and the explosive related:compounds of interest.

Therefore, the detector 10 may further comprise a first temperature control assembly 44 for regulating the temperature of the adsorption/desorption zone 40 of the capillary 13 so as to enhance selective adsorption/desorption of the molecules of the energetic compound. The detector 10 is also provided with a first temperature sensor 45 positioned adjacent to and/or within the capillary 13 for determining and outputting signals indicative of the temperature of the adsorption/desorption zone 40. The adsorption/desorption zone 40 may be maintained at a first temperature to effect adsorption of the molecules of the energetic compound and selectively elevated to a second temperature to effect desorption of the molecules of the energetic compound so as to form a pulse of desorbed molecules for passage to the sensing zone 42 of the capillary 13 by action of the carrier gas. The temperature ranges of the first and second temperatures of the adsorption/desorption zone 40 can vary, as long as the detector 10 functions in accordance with the present invention. Desirably, the first temperature is in the range of from about 10° Celsius above ambient temperature to about 15° Celsius above ambient temperature. Desirably, the second temperature is about 200° Celsius or above.

The time required for the shift between the first and second temperatures is critical. Generally, this shift occurs very quickly, preferably in less than about 3 seconds. However, a slower shift may be utilized, as a slower shift may be more selective than a faster shift, but a slower shift will also be less sensitive than a faster shift. The convertor assembly 30 indicates the presence of vapors of the energetic compound in the carrier gas at specific time intervals after receiving a timing signal indicative of the initiation of desorption of the molecules of the energetic compound from the adsorption/desorption zone 40 (i.e., the shift between first and second temperatures) and the signal from the light detector 28 indicating a change in emission intensity of the amplifying fluorescent polymer 32 of the sensing unit 24 at a predetermined time period after the reception of the timing signal by the convertor assembly 30.

Figure 5:
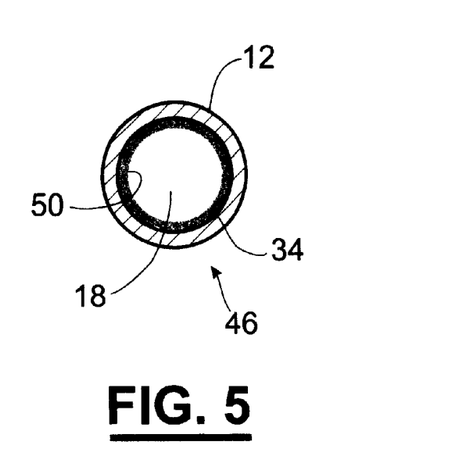

As shown in FIG. 5, the capillary 13 may further be characterized as having an equilibrium zone 46 positioned between the adsorption/desorption zone 40 and the sensing zone 42. The amplifying fluorescent polymer 32 is sensitive to temperature fluctuations, and in order to have low volatility explosive related compounds migrate through a segment of capillary 13, it is necessary to have the capillary, 13 at an elevated temperature. Yet in most cases, the carrier gas traveling from the inlet 20 through the adsorption/desorption zone 40 is at a temperature other than the temperature of the sensing zone 42. Therefore, if this carrier gas comes in contact with the amplifying fluorescent polymer 32, the amplifying fluorescent polymer 32 may be subjected to undesirable temperature fluctuations. This is exacerbated when the adsorption/desorption zone 40 is elevated to a second temperature to effect desorption of the vapors of the energetic compound. These temperature fluctuations can be considerably reduced if the carrier gas containing the analyte is passed through an equilibrium zone 46 prior to reaching the amplifying fluorescent polymer 32. This equilibrium zone 46 is a segment of capillary 13 located between the adsorption/desorption 40 and sensing zones 42 that is held at a fixed temperature. In most cases, the equilibrium zone 46 need be no longer than two to four centimeters. Over this distance, the carrier gas which may have temperatures ranging from 0° to 150° Celsius is brought to the temperature of the equilibration zone 46. It is important that the carrier gas striking the amplifying fluorescent polymer 32 not exceed the temperature required to thermally decompose the amplifying fluorescent polymer 32. Furthermore, the carrier gas striking the amplifying fluorescent polymer 32 must not exceed the temperature at which the plasticizer is removed or phase separates from the polymer 32.

Therefore, when the detector 10 is provided with an equilibrium zone 46, the detector 10 further comprises a second temperature control assembly 48 for maintaining the equilibrium zone 46 at a substantially constant temperature so as to condition the desorbed molecules and the carrier gas to the temperature of the equilibrium zone 46 The detector 10 is also provided with a second temperature sensor 47 positioned adjacent to and/or within the capillary 13 for determining and outputting signals indicative of the temperature of the equilibrium zone 46. The temperature of the equilibrium zone 46 should be cool enough to allow some interaction between the analytes and the coating 50 of the equilibrium zone 46 but still allow the analytes to move through the equilibrium zone 46 relatively stably and quickly. Desirably, the temperature of the equilibrium zone 46 is in the range of from about 60 E Celsius to about 150° Celsius.

The length of the equilibrium zone 46 can vary widely and depends on several parameters. The rate of migration of analyte through the equilibrium zone 46 depends on the same parameters as the adsorption/desorption zone 40, which has been described herein before. The equilibrium zone 46 must also be long enough that analyte exiting such zone 46 always exits at the same temperature regardless of the temperature of the gas entering it. Preferably, the equilibrium zone 46 is in the range of from about 20 mm to about 40 mm in length in order to achieve thermal equilibrium.

Just as the temperature and length of the equilibrium zone 46 is critical, the selection of coating 50 for the equilibrium zone 46 is also critical. The equilibrium zone 46 may be coated with a gas chromatographic stationary phase such as mixtures of dimethylpolysiloxane and diphenylpolysiloxane in various ratios. Alternatively, the equilibrium zone 46 may be coated with alkyl silanes, such as octadecyltrichlorosilane (OTS), 1,1,1,3,3,3-hexamethyldisilane (HMDS) and decyltrichlorosilane. The coating 50 of the equilibrium zone 46 may be the same or different than the coating 38 of the adsorption/desorption zone 40.

Figure 6:
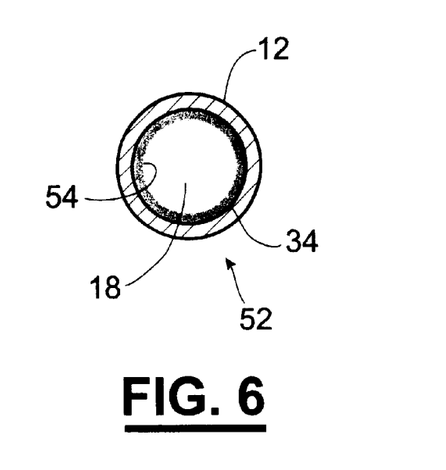

As shown in FIG. 6, the capillary 13 may further be characterized as having a chromatography zone 52 positioned between the adsorption/desorption zone 40 and the equilibrium zone 46. In essence, the chromatography zone 52 is configured as a short column gas chromatograph for separating multiple components or analytes into individual analytes or parts. The chromatography zone 52 is an enhancement to the adsorption/desorption zone 40, enabling further discrimination of target analytes from interferents. When the temperature of the adsorption/desorption zone 40 is rapidly increased after a sampling cycle, the molecules trapped in the adsorption/desorption zone 40 during sampling are introduced almost simultaneously into the chromatography zone 52 as a pulse of desorbed molecules. As described previously for the adsorption/desorption zone 40, molecules of different types migrate through the chromatography zone 52 in much the same way as through the adsorption/desorption zone 40, at rates determined by the strength of interaction of each type of molecule with the coating 54 in the chromatography zone 52. Since each component of the sample matrix moves through the chromatography zone 52 at a different rate, they will emerge from the exit of the chromatography zone 52 at different times. Each separated component then moves sequentially through the equilibrium zone 46 and into the sensing zone 42. The temperature of the chromatography zone 52 can also be varied, if desired. The detector 10 is provided with a fourth temperature control assembly 53a and a fourth temperature sensor 53b for permitting adjustment or changes to the temperature in the chromatography zone 52. That is, the fourth temperature control assembly 53a and fourth temperature sensor 53b are positioned adjacent to, on and/or within the capillary 13 for determining and changing the temperature of the chromatography zone 52.

The convertor assembly 30 then determines the presence of vapors of the energetic compound delivered by the carrier gas at specific time intervals after receiving a timing signal indicative of the initiation of desorption of the molecules of the energetic compound from the adsorption/desorption zone 40 and the signal from the light detector 28 indicating a change in emission intensity of the amplifying fluorescent polymer 32 of the sensing unit 24 at a predetermined time period after the reception of the timing signal by the convertor assembly 30. This predetermined time period is known as the 'retention time' for the energetic compound. Each energetic compound will have a characteristic retention time, and these retention times will likely differ.from the retention times for potentially interfering compounds. In this way it is possible to discriminate, based on retention times, interfering compounds from energetic materials.

The chromatography zone 52 is typically coated with a coating 54 including, but not limited to polydimethylsiloxane, diphenyl, cyanopropylphenyl, trifluoropropyl, and polyethylene glycol. The temperature range in the chromatography zone 52 can be varied in a predetermined manner with a temperature program running on a microcontroller 74 so as to aid in the separation of the components or analytes. Temperature programs for gas chromatographs are known in the art. Thus, no further comments are deemed necessary to teach one skilled in the art to make or use the temperature programs. The temperature in the chromatography zone 52 can desirably vary from about 40° C. to about 250° C. Ramp rates for varying the temperature are preferably variable and from about 5° C. per minute to about 80° C. per minute.

It is in this zone 52 that chromatographic separation occurs, so the zone 52 must be long enough to achieve the desired degree of chromatographic separation of analytes. If the chromatographic zone 52 is too short, resolution will be poor and interferent rejection will be difficult. If the chromatographic zone 52 is too long, the length of time required to analyze a sample will be long. The length of the chromatography zone 52 is preferably in the range of from about 4 inches to about 1 meter. However, it should be understood that the chromatography zone 52 can be provided with any shape or size so long as the chromatography zone 52 serves as a gas chromatograph. For example, the chromatography zone 52 can be, formed by a straight or a coiled tube.

Figure 7:
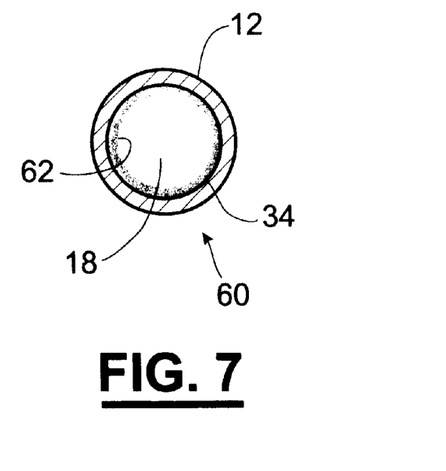

Referring to FIG. 7, the capillary 13 may be further characterized as having a preconditioning zone 60 or "inlet zone" positioned upstream of the adsorption/desorption zone 40 for gathering and feeding the vapors of the energetic compound present in the sample to the adsorption/desorption zone 40 of the capillary 13 at a predetermined rate. The preconditioning zone 60 of the capillary 13 may be constructed of fused silica having an effective amount of low-retention coating on an interior surface thereof to gather and feed the vapors of the energetic compound present in the sample to the adsorption/desorption zone 40 of the capillary 13 at the predetermined rate. The preconditioning zone 60 is typically coated with a non-retentive coating 62 including, but not limited to, various alkyl silanes, such as octadecyltrichlorosilane (OTS), 1,1,1,3,3,3-hexamethyldisilazane (HMDS) and decyltrichlorosilane.

The length of the preconditioning zone 60 is less critical than the length of the adsorption/desorption zone 40, the chromatographic zone 52, the equilibrium zone 46, or the sensing zone 42. The length of the preconditioning zone 60 should be kept as short as mechanically possible. The length of the preconditioning zone 60 is preferably in the range of from about 1 inch to about 5 inches. A fifth temperature control assembly 61a and a fifth temperature sensor 61b are provided for regulating the temperature of the preconditioning zone 60.

The fifth temperature sensor 61 is positioned adjacent to and/or within the capillary 13 for determining and outputting signals indicative of the temperature of the adsorption/desorption zone 40. The temperature of the preconditioning zone 60 should be high enough to prevent adsorption of the analyte. Desirably, the temperature of the preconditioning zone 60 will be in the range of from about 90 degrees to about 250 degrees Celsius.

The detector 10 may also comprise a third temperature control assembly 64 for maintaining the sensing zone 42 of the capillary 13 at a substantially constant temperature. The detector 10 is also provided with a third temperature sensor 65 positioned adjacent to and/or within the capillary 13 for determining and outputting signals indicative of the temperature of the sensing zone 42.

In operation, it is advantageous to use the capillary 13 as a gas chromatograph in order to improve sensor selectivity. It is important to introduce the analyte in a sharp, short-duration pulse in order to accurately determine the time required for an analyte to reach the sensing unit 24 at the end of the capillary 13. In order to do this, sample is drawn into the capillary 13 through a short, cooled length of capillary 13, or the adsorption/desorption zone 40. The lower the temperature of the capillary walls 34 in the adsorption/desorption zone 40, the more strongly analytes are retained on the walls 34. Because the short length of capillary 13 is cooled, the migration rate of analytes through the adsorption/desorption zone 40 of the capillary 13 is low. This enables sample to be drawn into the adsorption/desorption zone 40 for long periods of time without the analalyte migrating out of the adsorption/desorption zone 40. Hence, it is possible to extract analyte from a large volume of sample onto the walls of the adsorption/desorption zone 40 (or "trap zone"), making the concentration of analytes in the sample larger (i.e., sample 'preconcentration' occurs). At the appropriate time, the temperature of the adsorption/desorption zone 40 is rapidly increased. As the temperature of the adsorption/desorption zone 40 rises, the analytes migrate through the previously cooled length of capillary 13 at a high velocity. The sharp analyte pulse then enters the cooler length of capillary 13, the chromatographic zone 52. The analyte then begins to migrate through the chromatographic zone 52 at the velocity characteristic of the analyte and system parameters. The analyte then enters the equilibrium zone 46, where it reaches the temperature of the equilibrium zone 46 before exiting into the sensing zone 42 at precisely measured elapsed times from the instant the adsorption/desorption zone 40 is heated (i.e., "flashed").

Different analytes entering the capillary 13 at exactly the same instant will reach the sensing unit 24 at the opposite end of the capillary 13 at different times. If the analyte is introduced into the capillary 13 from the trap zone (i.e., the adsorption/desorption zone) 40 as a sharp, short duration pulse, the time elapsed between introduction of this analyte pulse and the time until the sensing assembly 16 responds can be used to help identify the analyte. For example, if the sensing assembly 16 responds to a sample, but the response is at the wrong time after sample introduction, the response is due to an interferent and not the target analyte. This provides a secondary means of discriminating target analytes from chemical interferents.

It has already been established that the analyte tends to form a moving annulus adhering to the surface of the interior wall 34 of the capillary 13 as it is moved towards the amplifying fluorescent polymer 32 in the sensing zone 42. Since the amplifying fluorescent polymer 32 is chosen to specifically interact with the analyte of interest, the migration rate of the analyte along the surface of the amplifying fluorescent polymer 32 is somewhat decreased by comparison with the less retentive coating 54 in the chromatographic zone 52 and the coating 50 in the equilibrium zone 46. The spatial extent of the analyte annulus is therefore decreased at the amplifying fluorescent polymer 32. To optimize the contrast engendered by adsorption of the analyte on the amplifying fluorescent polymer 32 it is best to limit the length of the amplifying fluorescent polymer 32 segment to the length of the compressed analyte annulus. If this is not done, there will be regions of the amplifying fluorescent polymer 32 which are emitting regardless of the location of the analyte annulus within the confines of the amplifying fluorescent polymer 32. This background emission is never quenched. If such background emission is present, the fraction of the total emission from the amplifying fluorescent polymer that may be quenched is lessened. To optimize the effect of quenching due to analyte, this background emission must be removed. This is best achieved by placing the amplifying fluorescent polymer 32 in a short band on the inside of the capillary 13 in the sensing zone 42. The length of this short band should be equal to the length of the annulus of analyte on the amplifying fluorescent polymer.

Methods of deploying amplifying fluorescent polymer over short lengths of capillary 13 have been developed. These short 'bands' of polymer improve sensitivity compared to longer bands of polymer. In essence, short bands improve the contrast of the sensing unit 24. However, smaller bands result in less signal, so if the band becomes too narrow, the signal-to-noise ratio is degraded.

The band of amplifying fluorescent polymer 32 provided on an internal surface 34 of the capillary 13 in the sensing zone 42 has a width sufficient to capture the desorbed vapors while substantially preventing the desorbed vapors from passing over the band of amplifying fluorescent polymer 32 without adsorption. The width of the band of amplifying fluorescent polymer 32 is in a range of from about 0.5 mm to about 3 mm, and preferably in a range of from about 1 mm to about 2 mm. The thickness of the band of amplifying fluorescent polymer 32 should be in the range of from about 1 molecular layer to about 20 molecular layers, and preferably in the range of from about 10 molecular layers to about 20 molecular layers. The number of molecular layers affects the responsivity and sensitivity of the polymer. Since many layers, perhaps up to fifteen layers, can transfer energy to the surface layer, a multilayer system will increase the number of photons absorbed which also result in quenching events. This improves the signal to noise ratio and sensitivity which are dependent on the number of photons emitted by the unquenched polymer. However, if the number of layers is much greater than this, the layers farthest from the surface will not be in electronic communication with the surface. They will emit light that cannot be quenched, resulting in decreased responsivity.

The length of the sensing zone 42 depends mainly (but not entirely) on the width of the analyte pulse as it leaves the equilibrium zone 46 and the migration rate of analyte across the sensing zone 42 (which again depends on temperature and flow rate). The length of the sensing zone 42 is preferably in the range of from about 0.5 mm to about 3 mm. The sensing zone 42 is preferably coated with alkyl silanes prior to deposition of the amplifying fluorescent polymer 32. Examples of alkyl silanes which may be utilized in accordance with the present invention include octadecyltrichlorosilane (OTS), 1,1,1,3,3,3-hexamethyldisilane (HMDS) and decyltrichlorosilane.

The capillary 13 forming the housing 12 may be purchased with the gas chromatographic stationary phase coated therein, and the silane or other layers may be applied using standard coating techniques. When a precoated capillary 13 is utilized, the coating in the sensing zone 42 may be removed by any method known in the art, such as by treatment with hot acid (such as sulfuric acid at about 130° Celsius), or by laser ablation. Alternatively, each of the zones may be formed in separate pieces of capillary 13, and the multiple pieces of capillary 13 containing each of the zones may be joined together to form a continuous length of capillary 13 by any method known in the art.

The amplifying fluorescent polymer formulation (either single polymers, mixtures of polymers, or plasticized polymers) may be applied to the capillary 13 by any method known in the art. Preferably, the amplifying fluorescent polymer formulation is applied to the capillary 13 by spin coating. In the spin coating method, two balanced capillaries are mounted on a spinner, such as the Photo Resist Spinner manufactured by Headway Research of Garland, Tex., model number 1-EC101-R485, and stops are placed on the ends to hold the capillaries on the spinner. An effective amount of amplifying fluorescent polymer formulation, such as in a range of from about 1 microliter to about 10 microliters, is placed in the end of each capillary, and the capillaries are spun, thereby causing the amplifying fluorescent polymer to be coated on the inner surface of the capillary. To remove excess amplifying fluorescent polymer (i.e., polymer coating the capillary at locations outside the desired narrow band of polymer), solvent is injected in each end of the capillary to rinse away the polymer coating. This results in a band of amplifying fluorescent polymer of a predetermined size and location in the capillary.

While the present embodiments described herein are provided with a coated capillary as the sensing unit 24, it will be understood that the present invention is not limited to the use of a coated capillary as the sensing unit, and other sensing units may be employed in the scope of the present invention. For example, the sensing unit 24 could be a bead or a plate waveguide (having the amplifying fluorescent polymer 32 thereon) inside of a defined volume such as the housing 12 or the capillary 13.

The first, second, third, fourth and fifth temperature control assemblies 44, 48, 64, 53a and 61a can be any devices capable of changing or varying the temperature as set forth above. For example, the first, second, third, fourth and fifth temperature control assemblies 44, 48, 64, 53a and 61a can be resistance heaters.

Turning now to the sensing assembly 16, any source of excitation 26 producing a medium that interacts with the amplifying fluorescent polymer 32 to cause the amplifying fluorescent polymer 32 to generate light may be used as long as the source functions in accordance with the present invention. Such source of excitation 26 is preferably a mode-locked light source, such as a UV LED or a blue LED, or a mode-locked laser, such as a blue laser diode. An example of a blue laser diode is made by Nichia, NLHV500A/B. Examples of blue LEDs (470 nm) are Panasonic LNG992CFBW, Panasonic LNG901CFBW and Panasonic LNG91LCFBW. Other sources of excitation 26 which may be used in accordance with the present invention include cold cathode lamps, ore lamps and tungsten lamps. Examples of UV cold cathode lamps are made by JKL and include BF325-UV1, BF350-UV1, BF3100-UV1, BF3120-UV1, BF3240-UV1, and BF959-UV1/3. The source of excitation 26 only illuminates the portion of the detector, 10 which contains the amplifying fluorescent polymer 32, such that the sensing zone 42 containing the amplifying fluorescent polymer 32 is the only portion of the capillary 13 which is illuminated.

The light source 26 must emit a wavelength of light such that the amplifying fluorescent polymer 32 can generate light when exposed to such wavelength of light. The wavelength of light emitted by the light source 26 is determined based on the specific amplifying fluorescent polymer 32 used. For the amplifying fluorescent polymers discussed herein, it has been found that a wavelength in the range of from about 300 nm to about 470 nm is desirable. However, the light source may have a second harmonic and therefore emit light at a wavelength in the range of from about 600 nm to about 1000 nm.

A blue diode laser, such as Nichia NLHV500A, may be utilized as the source of excitation 26, and may be positioned to throw a focused beam normal to the axis of the capillary tube 13 and illuminate the amplifying fluorescent polymer 32. The laser beam is preferably focused by a lens, and collection and focusing lenses may be provided between the capillary tube 13 and the light detector 28. The beam is electronically chopped by controlling its input current. The current is controlled by an automatic power control (APC) circuit alternately to either a high intensity, such as 4000 microwatts, or to a low intensity, such as 200 microwatts. The rate of switching alternately to the two power intensity levels is preferably 2225 or 2400 times per second. The laser beam intensity should be stable over time for both power levels, and should be free of power fluctuations, to the extent that the high power signal exceeds the noise level by 120 dB or more. The laser is preferably cooled, or alternately mounted in a massive heat sink which will slow the effects of its spectral output line hopping and its intensity monitoring photodetector sensitivity change to a rate which produces negligible effect during a measurement cycle.

The detector 10 may further comprise means for maintaining the temperature of the source of excitation 26 at a predetermined temperature. The predetermined temperature of the source of excitation 26 is maintained at a temperature of about 25 degrees Centigrade.

The detector 10 may comprise a first filter 66 positioned between the source of excitation 26 and the sensing unit 24 so as to block light in a wavelength range corresponding to the wavelength of light generated by the amplifying fluorescent polymer 32, and to pass only the light over the range of wavelengths emitted by the source of excitation 26 that result in excitation of the amplifying fluorescent polymer 32. Examples of filters which may be used in accordance with the present invention can be purchased from Corion, such as LS-450, S25-400, P10-370 and XM-360, or from Optometrics Group, such as 2-4304 and 2-4364.

The light detector 28 may be any detector which can sense light of the wavelength emitted by the amplifying fluorescent polymer 32. The light detector 28 may be a charge-coupled device (CCD), a photomultiplier tube (PMT), a photodiode or a pyrometer. Preferably, the light detector 28 is a photomultiplier tube or photodiode.

In one embodiment, a sensitive, linear photo detector with a wide dynamic range such as the H5784 photomultiplier tube (PMT) by Hamamatsu of Japan is positioned normal to the second end of the capillary tube 13 and function's as the light detector 28 of the sensing assembly 16 of the detector 100. The detector 10 may also comprise means for maintaining the light detector 28 at a predetermined temperature. The predetermined temperature of the light detector 28 is maintained at a temperature of about 35 degrees Centigrade.

A second filter 68 may be positioned between the sensing unit 24 and the light detector 28 for passing light generated by the amplifying fluorescent polymer 32 and for blocking the medium emitted by the source of excitation 26. The filter 68 is selected to prevent laser light from reaching the photo detector 28, and it may preferably also block a significant amount of stray light from the environment. The polymer's fluorescent emission must pass through the filter 68. Examples of filters which may be used as the second filter 68 in accordance with the present invention can be purchased from Corion, such as LL-450, LL-500, S40-500, S25-500, XM-485 and XM-465, or from Optometrics Group, such as 2-4584, 2-4924 and 2-5004.

The source of excitation 26 is modulated at a predetermined frequency, and the converter assembly 30 demodulates the signal from the light detector 28 at the predetermined frequency. In this manner, only signals in the signal from the light detector 28 which have been produced directly by the amplifying fluorescent polymer 32 and indirectly from the medium produced by the source of excitation 26 will be recovered.

The photodetector's 26 electrical output is received by a synchronous detector 70 which is synchronized to the laser chop signal. The synchronous detector 70 extracts the desired chopped fluorescence signal from light noise, particularly stray light from the environment. The noise free dynamic range of the synchronous detector 70 should preferably be in excess of 120 dB. Its output is through a low-pass filter of at least third order with a cut-off point of preferably about one-half Hertz. The result is a DC signal which represents the polymer's fluorescence in response to laser excitation. The synchronous detector 70 may be implemented in either analog or digital circuitry, or by a combination of the two. It is important that components are used which are insensitive to thermal variations or that have a very small thermal reaction. For example, it is preferable to use resistors with about 10 ppm/° C. or less change in resistance as a function of temperature.

An analog-to-digital converter 72 digitizes the DC signal which it receives from the synchronous detector 70, preferably with a noise free dynamic range of at least 120 dB. It is monitored and controlled by the microcontroller 74 such as a PLC, which also may measure or control other functions of the system. The microcontroller 74 can be used in combination with a digital signal processor, or a logic control unit to provide additional processing power and efficiency. The microcontroller 74 can be a "microcontroller", a digital signal processor, a logic control unit or other type of processing device capable of carrying out the functions set forth herein.

The microcontroller 74 passes digitized information to an external computer, such as an HP200LX palm top computer for storage and output. The computer may output a graph and/or log of data points 76 which an operator can use to determine presence or absence of the analyte.

An air pump 14, such as Schwarzer Precision model SP 135 FZ, draws air through the capillary 13 and past the amplifying flourescent polymer 32 of the sensing unit 24. The detector 10 may also be provided with a flow meter 78 which receives the carrier gas and determines the flow rate of the carrier gas. Airflow is controlled to a constant preset rate such as about 60 ml/min using a mass airflow sensor such as Honeywell AWM3100V. A microcontroller 74 will preferably implement a closed control loop for airflow, and allow desired flow settings. Pulsations in airflow will preferably be reduced by pneumatic filtering effected by an expandable volume in latex tubing, and an orifice.

The invention is not limited to finding land mines or nitroaromatic compounds. It is designed to be adapted to other analytes by changing polymers in the capillary tube.

From the above description, it is clear that the present invention is well adapted to carry out the objects and to attain the advantages mentioned herein as well as those inherent in the invention. While presently preferred embodiments of the invention have been described for purposes of this disclosure, it will be understood that numerous changes may be made which will readily suggest themselves to those skilled in the art and which are accomplished within the spirit of the invention disclosed and as defined in the appended claims.

What is claimed is:

1. A detector for detecting vapors emitted from energetic compounds present in a sample, comprising:

a housing defining an enclosed sensing volume, the housing having an inlet and an outlet communicating with the enclosed sensing volume such that a carrier gas can be moved sequentially through the inlet, the enclosed sensing volume and the outlet;

a pump communicating with the housing for moving the carrier gas sequentially through the enclosed sensing volume at a predetermined flow rate; and a sensing assembly for sensing the vapors of the energetic compound delivered by the carrier gas as the carrier gas passes through the housing, the sensing assembly comprising:

a sensing unit constructed of an amplifying fluorescent polymer positioned in the housing so as to be openly communicating with the enclosed sensing volume of the housing, wherein the intensity of light emitted by the amplifying fluorescent polymer varies in response to interaction of the amplifying fluorescent polymer with molecules of the energetic compound delivered by the carrier gas;

a source of excitation producing a medium that interacts with the amplifying fluorescent polymer to cause the amplifying fluorescent polymer to generate light;

a light detector positioned to receive the light generated by the amplifying fluorescent polymer, the light detector outputting a signal indicative of the intensity of the light generated by the amplifying fluorescent polymer; and a converter assembly receiving the signal from the light detector and converting such signal into a format perceivable by an individual.

2. The detector of claim 1, wherein the housing is a capillary characterized as having an adsorption/desorption zone and a sensing zone with the sensing zone being downstream from the adsorption/desorption zone, the capillary in the adsorption/desorption zone selectively adsorbing and desorbing at least a portion of the molecules of the energetic compound delivered in the carrier gas, and the sensing unit of the sensing assembly being positioned in the sensing zone of the capillary for detection of molecules of the energetic compound.

3. The detector of claim 2, further comprising a first temperature control assembly for regulating the temperature of the adsorption/desorption zone of the capillary so as to enhance selective adsorption/desorption of the molecules of the energetic compound.

4. The detector of claim 3, wherein the adsorption/desorption zone is maintained at a first temperature to effect adsorption of the molecules of the energetic compound and selectively elevated to a second temperature to effect desorption of the molecules of the energetic compound so as to form a pulse of desorbed molecules for passage to the sensing zone of the capillary by action of the carrier gas.

5. The detector of claim 4, wherein the converter assembly indicates the presence of vapors of the energetic compound delivered by the carrier gas at specific time intervals after receiving a timing signal indicative of the initiation of desorption of the molecules of the energetic compound from the adsorption/desorption zone and the signal from the light detector indicating a change in emission intensity of the amplifying fluorescent polymer of the sensing unit at a predetermined time period after the reception of the timing signal by the converter assembly.

6. The detector of claim 2, wherein the capillary is further characterized as having an equilibrium zone positioned between the adsorption/desorption zone and the sensing zone, and wherein the detector further comprises a second temperature control assembly for maintaining the equilibrium zone at a substantially constant temperature so as to condition the desorbed molecules and the carrier gas to the temperature of the equilibrium zone.

7. The detector of claim 6, wherein the detector further comprises a third temperature control assembly for maintaining the sensing zone of the capillary at a substantially constant temperature.

8. The detector of claim 2, wherein the capillary is further characterized as having a preconditioning zone positioned upstream of the adsorption/desorption zone for gathering and feeding the vapors of the energetic compound present in the sample to the adsorption/desorption zone of the capillary at a predetermined rate.

9. The detector of claim 8, wherein the preconditioning zone of the capillary is constructed of fused silica having an interior surface coated with an effective amount of a low-retention coating to gather and feed the vapors of the energetic compound present in the sample to the adsorption/desorption zone of the capillary at the predetermined rate.

10. The detector of claim 2, wherein the sensing unit includes a plurality of bands of different amplifying fluorescent polymers coated onto an internal surface of the capillary, each band being illuminated by a light source of distinct wavelength and modulation frequency, and each band having a width sufficient to capture the desorbed molecules while substantially preventing the desorbed molecules from passing over the band of amplifying fluorescent polymer without adsorption.

11. The detector of claim 2, wherein the sensing unit includes a band of the amplifying fluorescent polymer coated onto an internal surface of the capillary, the band having a width sufficient to capture the desorbed molecules while substantially preventing the desorbed molecules from passing over the band of amplifying fluorescent polymer without adsorption.

12. The detector of claim 11, wherein the width of the band of amplifying fluorescent polymer is in a range from about 0.5 mm to about 3 mm.

13. The detector of claim 1, further comprising a first filter positioned between the source of excitation and the sensing unit so as to block light in a wavelength range corresponding to the wavelength of light generated by the amplifying fluorescent polymer, and to pass only the light over the range of wavelengths emitted by the source of excitation that result in excitation of the amplifying fluorescent polymer.

14. The detector of claim 13, further comprising a second filter positioned between the sensing unit and the light detector passing light generated by the amplifying fluorescent polymer and for blocking the medium emitted by the source of excitation.

15. The detector of claim 1, wherein the source of excitation is modulated at a predetermined frequency, and the converter assembly demodulates the signal from the light detector at the predetermined frequency so as to only recover signals in the signal from the light detector which have been produced directly by the amplifying fluorescent polymer and indirectly from the medium produced by the source of excitation.

16. The detector of claim 1, wherein the amplifying fluorescent polymer contains an effective amount of a plasticizing material so as to reduce photodecomposition of the amplifying fluorescent polymer and thereby extend the useful life of the amplifying fluorescent polymer.

17. The detector of claim 16, wherein the plasticizing material is dioctylphthalate.

18. The detector of claim 1, wherein the pump draws the carrier gas sequentially through the inlet, enclosed sensing volume and the outlet of the housing.

19. The detector of claim 1, further comprising a flow meter receiving the carrier gas and determining the flow rate of the carrier gas.

20. The detector of claim 1, further comprising means for maintaining the temperature of the source of excitation at a predetermined temperature.

21. The detector of claim 20, wherein the predetermined temperature of the source of excitation is maintained at a temperature of about 25° Celsius.

22. The detector of claim 1, further comprising means for maintaining the temperature of the light detector at a predetermined temperature.

23. The detector of claim 22, wherein the predetermined temperature of the light detector is maintained at a temperature of about 35° Celsius.

* * * * *

UNITED STATES PATENT AND TRADEMARK OFFICE
CERTIFICATE OF CORRECTION

PATENT NO. : 6,558,626 B1
DATED : May 6, 2003
INVENTOR(S) : Aker et al.

It is certified that error appears in the above-identified patent and that said Letters Patent is hereby corrected as shown below:

Drawings,
FIG. 2, please delete numeral "43" and substitute therefor -- 52 --.
FIG. 2, please insert numeral -- 13 -- and its associated lead line.
FIG. 2, please insert numeral -- 45 -- and its associated lead line.
FIG. 2, please insert numeral -- 47 -- and its associated lead line.
FIG. 2, please insert numeral -- 53a -- and --53b -- and each associated lead line.
FIG. 2, please insert numeral -- 61a -- and -- 61b -- and each associated lead line.
FIG. 2, please insert the numeral -- 65 -- and its associated lead line.

FIG. 2

Column 3,
Line 6, delete "Aanalyte" and substitute therefor -- Analyte --.
Line 60, delete "If or" and substitute therefor -- for --.

Column 4,
Line 65, delete "polymethylacrylate" and substitute therefor -- polymethylmethylacrylate --.

Column 10,
Line 20, delete "related:compounds" and substitute therefor -- related compounds --.

UNITED STATES PATENT AND TRADEMARK OFFICE
CERTIFICATE OF CORRECTION

PATENT NO. : 6,558,626 B1
DATED : May 6, 2003
INVENTOR(S) : Aker et al.

It is certified that error appears in the above-identified patent and that said Letters Patent is hereby corrected as shown below:

Column 11,
Line 40, delete "60 E Celsius" and substitute therefor -- 60 Celsius --.
Line 59, delete "hexamethyldisilane" and substitute therefor
-- hexamethyldisilazane --.

Column 13,
Line 34, delete "61" and substitute therefor -- 61b --.

Column 15,
Line 31, delete "hexamethyldisilane" and substitute therefor
-- hexamethyldisilazane --.

Column 17,
Line 28, delete "100" and substitute therefor -- 10--.

Signed and Sealed this

Twenty-fourth Day of August, 2004

JON W. DUDAS
*Director of the United States Patent and Trademark Office*

UNITED STATES PATENT AND TRADEMARK OFFICE
CERTIFICATE OF CORRECTION

PATENT NO. : 6,558,626 B1
DATED : May 6, 2003
INVENTOR(S) : Craig A. Aker et al.

It is certified that error appears in the above-identified patent and that said Letters Patent is hereby corrected as shown below:

Column 1,
Line 12, delete "Not Applicable" and add -- Portions of the invention were developed under Contract Number: DAAD 16-00-C-9242, Contracting Office: U.S. Army AMCAC Natick Contracting Division, Project Title: "Dog's Nose Project.--

Signed and Sealed this

Twelfth Day of October, 2004

JON W. DUDAS
*Director of the United States Patent and Trademark Office*